US006898337B2

(12) United States Patent
Averett et al.

(10) Patent No.: US 6,898,337 B2
(45) Date of Patent: May 24, 2005

(54) FIBER-OPTIC APPARATUS AND METHOD FOR MAKING SIMULTANEOUS MULTIPLE PARAMETER MEASUREMENTS

(75) Inventors: Joshua P. Averett, Radford, VA (US); Jennifer L. Elster, Blacksburg, VA (US); Mark E. Jones, Blacksburg, VA (US); Charles D. Pennington, Blacksburg, VA (US); Roger L. Van Tassell, Blacksburg, VA (US)

(73) Assignee: Luna Innovations, Incorporated, Blacksburg, VA (US)

( * ) Notice: Subject to any disclaimer, the term of this patent is extended or adjusted under 35 U.S.C. 154(b) by 0 days.

(21) Appl. No.: 10/805,081

(22) Filed: Mar. 19, 2004

(65) Prior Publication Data

US 2004/0218847 A1 Nov. 4, 2004

Related U.S. Application Data

(60) Provisional application No. 60/455,470, filed on Mar. 19, 2003.

(51) Int. Cl.[7] .............................. G02B 6/26; G02B 6/34
(52) U.S. Cl. .......................................... 385/12; 385/37
(58) Field of Search .......................................... 385/12

(56) References Cited

U.S. PATENT DOCUMENTS

| | | | |
|---|---|---|---|
| 5,430,817 A | | 7/1995 | Vengsarkar |
| 5,641,956 A | * | 6/1997 | Vengsarkar et al. ... 250/227.14 |
| 5,864,641 A | | 1/1999 | Murphy et al. |
| 6,021,240 A | | 2/2000 | Murphy et al. |
| 6,035,082 A | | 3/2000 | Murphy et al. |
| 6,058,226 A | | 5/2000 | Starodubov |
| 6,275,628 B1 | | 8/2001 | Jones et al. |
| 6,343,168 B1 | | 1/2002 | Murphy et al. |
| 6,366,722 B1 | | 4/2002 | Murphy et al. |
| 6,542,668 B2 | * | 4/2003 | Gaylord et al. ............... 385/37 |
| 6,576,430 B1 | | 6/2003 | Hsieh et al. |
| 2003/0130167 A1 | | 7/2003 | Pitner et al. |

OTHER PUBLICATIONS

Martin, Jennifer E., "Composite Films for Modifying Evanescent Wave Characteristics in Long–Period Grating Biosensors," Feb. 9, 2001, Virginia Polytechnic Institute and State University, pp. 39–40.*

Bhatia, Vikram, "Applications of Long–Period Gratings to Single and Multi–Parameter Sensing," Corning Incorporated, 1999 Optical Society of America, pp. 2–10.*

T.A. Tran, et al., "Real–Time Immunoassays Using Fiber–Optic Long–Period Grating Sensors," SPIE, Jan. 1996, p. 165–170, vol. 2676.

(Continued)

*Primary Examiner*—John D. Lee
*Assistant Examiner*—James D. Stein
(74) *Attorney, Agent, or Firm*—Joy L. Bryant (57) ABSTRACT

A fiber-optic method for making simultaneous multiple parameter measurements employs an optical fiber sensor having at least one long period grating disposed therein. An excitation is created in the optical fiber sensor wherein a plurality of evanescent field sensing depths result. At least two long period grating signatures are created. When the optical fiber sensor is exposed to at least one material, changes in the material are identified by simultaneously measuring and comparing shifts in each long period grating signature; correlating the shifts to changes in the material; and solving a series of equations that compare changes in the coupling wavelength for a specific loss band. A reactive coating may be applied to the optical fiber sensor proximate to the long period grating such that changes in the reactive coating as it reacts with the material may also be monitored.

32 Claims, 8 Drawing Sheets

OTHER PUBLICATIONS

A.M. Vengsarkar et al., "Long–Period Fiber Gratings As Band–Rejection Filters," Optical Fiber Communication '95, Feb. 26–Mar. 3, 1995, pp. PD4–1—PD4–5.

A.M. Vengsarkar et al., "Long–Period Fiber Gratings As Gain–Flattening And Laser Stabilizing Devices," Tenth International Conference on Integrated Optics and Optical Fibre Communication, Jun. 26–30, 1995, pp. 3–4, vol. 5, Hong Kong.

A.M. Vengsarkar et al., "Long–Period Fiber Gratings as Band–Rejection Filters," Journal of Lightwave Technology, Jan. 1996, pp. 58–65, vol. 14, No. 1.

A.M. Vengsarkar et al., "Long–Period Cladding–Mode–Coupled Fiber Gratings: Properties and Applications," Technical Digest Series, Sep. 9–11, 1995, pp. SaB2–1—SaB2–4, vol. 22.

V. Bhatia et al., "Optical Fiber Long–Period Grating Sensors," Lightnews, Winter 1995, pp. 6–11.

* cited by examiner

FIBER-OPTIC APPARATUS AND METHOD FOR MAKING SIMULTANEOUS MULTIPLE PARAMETER MEASUREMENTS

CROSS-REFERENCE TO RELATED APPLICATIONS

This application claims the benefit of U.S. Provisional Patent Application Ser. No. 60/455,470, entitled "Optical Fiber Sensor Arrangement for Multiple Parameter Measurement," filed Mar. 19, 2003, which is hereby incorporated by reference in its entirety.

FIELD OF THE INVENTION

The present invention relates to a fiber-optic method and apparatus for making simultaneous multiple parameter measurements. In particular, the invention is directed towards measuring and comparing shifts in long period grating signatures as an optical fiber is exposed to a material and correlating such shifts to various changes in the material.

BACKGROUND OF THE INVENTION

It is often desirable to have the ability to measure changes in materials as they undergo various chemical and biological reactions in real time. Direct detection is one method employed for such measurements and is typically based on optical techniques that respond to changes in refractive index. The optical response has been attributed strictly to mass capture as molecules are bound to the sensor surface.

Hsieh et al. (U.S. Pat. No. 6,576,430 B1) describe a method for detecting and analyzing allosteric receptor/ligand binding by monitoring changes in the surface refractive index. They found that changes in refractive index can be used to detect binding of ligands to immobilized receptors when the receptor (e.g., a binding protein) or the receptor-surface complex undergoes a conformational change upon binding to the ligand. The conformational change is detectable even when the ligand is small and the receptor is large. By employing Surface Plasmon Resonance (SPR) techniques, they found that binding of such allosteric binding agents to their ligands may produce negative deviations in the optical response or a decrease in resonance angle. Alternatively, they also found that an increase in refractive index was observed for allosteric binding agents which "open" upon binding of their ligands, resulting in a positive deviation in the optical response. By observing these deviations, they are able to detect receptor/ligand binding even when the ligand is small. When employing similar techniques in long period grating (LPG) systems, they observed an opposite result from that of SPR. They concluded that changes observed on LPG do not always follow those observed on SPR. This method is limited to single sensing depths because only one polarization state can transfer energy into the metallic layer of the SPR sensor. In the case of a LPG system, only one binding depth could be detected and there was no way to distinguish between different parameters. Thus, when there are changes in two parameters occurring simultaneously, such as protein shape (density) and mass capture, these changes cannot be separately distinguished.

Murphy et al. (U.S. Pat. No. 5,864,641) disclose an optical fiber long period sensor having a reactive coating. The reactive coating is positioned in an operable relationship to the long period grating and causes the long period grating to produce a wavelength transmission spectrum functionally dependent on a parameter sensed. When the chemically reactive coating has target sites present, a chemical bond is formed between the target site and the specific molecule. This causes a change in the wavelength transmission spectrum produced by the long period grating. The coatings and the positional relationship of the coating with respect to the long period grating sensor described by Murphy et al. are suitable for use in practice of the present invention.

Pitner et al. (U.S. Patent Application Publication 2003/0130167 A1) modified the sensor of Murphy et al. such that the affinity coating contained mutated proteins capable of detecting binding between analyte and mutated Galactose/Glucose Binding Protein. The modified sensor was used to measure refractive index changes as binding occurred. However, such changes were still limited to single parameter measurements.

An object of the present invention is to provide a fiber-optic method for making simultaneous multiple parameter measurements using an optical fiber having at least one long period grating.

Another object of the present invention is to provide a way to identify changes in a reactive coating as it reacts with a material by correlating shifts in at least two different long period grating signatures with changes in the material and solving a series of equations.

Another object of the present invention is to provide a method for identifying changes in a material as it is applied to a surface of an optical fiber sensor by comparing shifts in at least two long period grating signatures, correlating the shifts to changes in the material, and solving a series of equations.

SUMMARY OF THE INVENTION

The present invention is directed toward a fiber-optic method for making simultaneous multiple parameter measurements. For the purpose of this application, simultaneous is defined as having the ability to make two independent measurements at the same time. In practicing the method, an optical fiber sensor comprising at least one optical fiber having at least one long period grating disposed therein and having at least one reactive coating disposed thereon proximate to the long period grating is employed. An excitation in the optical fiber sensor is created causing a plurality of evanescent field sensing depths to result and creating at least two long period grating signatures correlated to separate and distinct or different sensing depths. The optical fiber sensor is exposed to at least one material. Changes in the reactive coating as it reacts with the material are identified by measuring and comparing shifts in each long period grating signature; correlating the shifts to the changes in the material; and solving a series of equations that compare the changes in the coupling wavelength for a specific loss band.

An alternative method of the present invention does not employ a reactive coating. The changes measured by this method are restricted to thickness measurements or thickness changes and refractive index changes.

An optical fiber sensing arrangement for practicing the method of the present invention is also described. The arrangement comprises at least one optical fiber having at least one long period grating disposed therein and at least one reactive coating disposed on the optical fiber proximate to the long period grating. A source means for launching light through the optical fiber is provided such that a plurality of evanescent field sensing depths results. A detector for detecting a coupling wavelength for a specific loss band is also provided. A means for solving a series of equations that compare changes in the coupling wavelength for a specific loss band is also provided.

Additional objects and advantages of the invention will be set forth in part in the description which follows, and in part will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principles thereof, and in which.

DETAILED DESCRIPTION OF THE PREFERRED EMBODIMENTS

The method of the present invention employs the technique of making simultaneous measurements of multiple parameters by using multiple sensing depths. As an optical fiber sensor is exposed to at least one material, changes in the material or in the reactive coating on the fiber are identified by measuring and comparing shifts in each long period grating signature; correlating the shifts to changes in the material; and solving a series of equations that compare changes in the coupling wavelength for a specific loss band. In essence, by simultaneously exciting at least two sensing depths outside the optical fiber using a long period grating device and solving a series of equations that compare changes in the coupling wavelength for a specific loss band, one is able to identify various changes occurring within a material or a reactive coating.

The method of the present invention employs an optical fiber sensor having at least one long period grating (LPG) disposed therein. Such sensors are known in the art and are described in U.S. Pat. No. 5,641,956 to Vengsarkar et al. which is hereby incorporated by reference in its entirety. As light is launched through the optical fiber, the long period grating couples the light from the guided modes (in the core) to the lossy non-guided modes (in the cladding). Based on the grating periodicity, a phase matching condition is satisfied such that the forward propagating fundamental mode is coupled into propagating cladding modes and the electric field extends out of the optical fiber. This field can extend up to one micron out of a typical 125-micron diameter optical fiber and is what creates the sensing region in the LPG sensor. The spectral location of the loss band due to this modal coupling is a function of the difference in the effective indices of the guided mode and the corresponding cladding mode. Thus, the long period grating produces a wavelength transmission spectrum functionally dependent on the physical parameter that is being sensed.

Alternatively, the optical fiber sensor has a reactive coating disposed thereon proximate to the long period grating. Such optical fiber sensors are described in U.S. Pat. No. 5,864,641 to Murphy et al. and is hereby incorporated by reference in its entirety. The reactive coating is capable of undergoing a change when exposed to a specific parameter such that it causes the long period grating to produce a wavelength transmission spectrum functionally dependent on the change which takes place.

In practicing the method of the present invention, it is necessary to be able to make simultaneous multiple sensing depth measurements. This is achieved by the optical fiber sensor having at least one long period grating disposed therein which causes a plurality of evanescent field depths to result when an excitation is created in the optical fiber sensor. The excitation creates at least two long period grating signatures. Each long period grating signature is defined by the equation:

$$\lambda = (n_g - n_{cl})\Lambda$$

wherein:

$\lambda$=coupling wavelength for a specific loss band $\Lambda$=grating period $n_g$=effective index of the guided mode of the optical fiber $n_{cl}$=effective index of a cladding mode of the optical fiber.

Figure 1A:
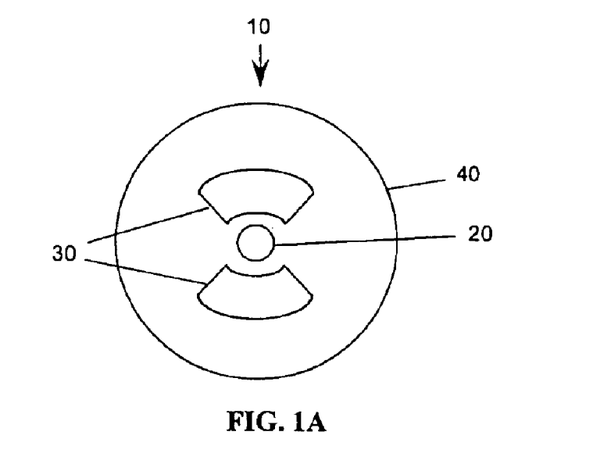
FIG. 1A depicts a cross-sectional view of the polarization preserving fiber.
Figure 1B:
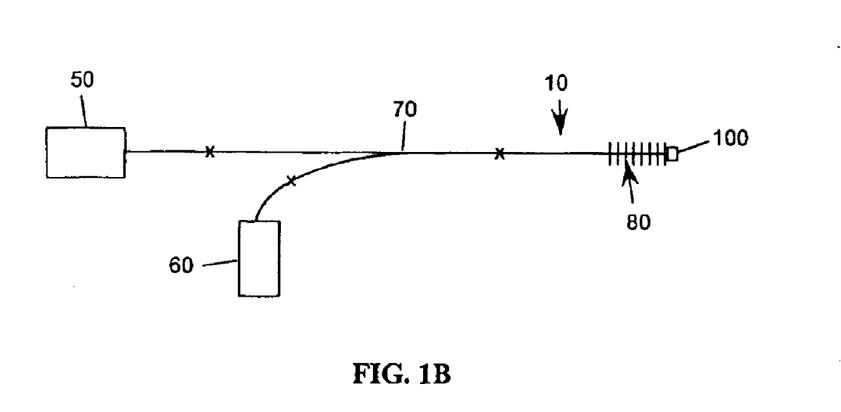
FIG. 1B depicts an optical fiber arrangement that employs a polarization preserving fiber having at least one long period grating disposed therein.
Figure 1C:
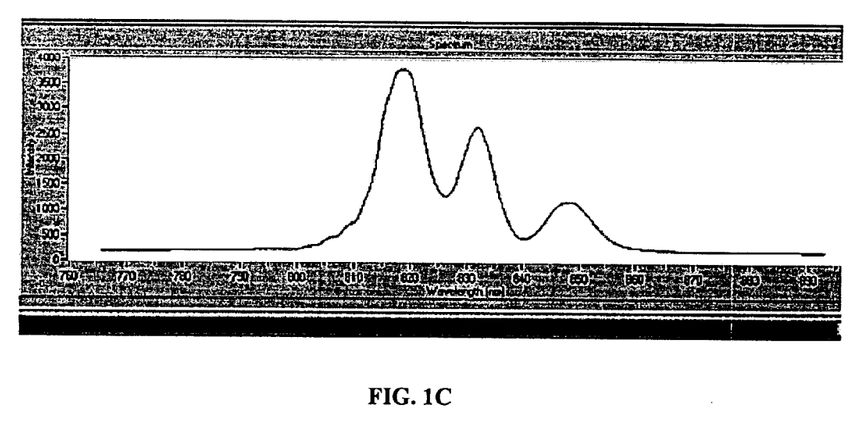
FIG. 1C depicts the long period grating signature produced by a polarization preserving fiber having at least one long period grating disposed therein.

In one embodiment of the invention, the optical fiber employed is a polarization preserving fiber, which is also known as a polarization maintaining fiber. FIG. 1A depicts a cross-sectional view of a polarization maintaining fiber 10 employed in the present invention. The fiber 10 consists of a core 20 surrounded by stress rods 30 which are encased in a cladding 40. When polarization maintaining fiber is used, a plurality of evanescent field depths result when light is launched through the fiber core 20 and reflected off of the stress rods 30. These evanescent field depths are situated at the site of the long period grating. Such polarization preserving fiber is a birefringent fiber that maintains polarization as light is launched into the fiber. This polarization enables one to sense two different depths at the same location. These sensing depths typically vary from one another by a depth of up to about 25%. Examples of such fiber include but are not limited to Panda Fiber, which is commercially available from Fujikura, and Tiger Fiber, which is commercially available from 3M. To monitor insitu reactions, the optical fiber has at least one reactive coating disposed thereon proximate to at least one long period grating. Measurements are made in real time as the material reacts with the reactive coating. As the reaction proceeds, each LPG peak shifts based on spatially resolvable density changes occurring within the material. FIG. 1B depicts an optical arrangement that employs the polarization maintaining fiber 10. The arrangement consists of an optical source 50, a spectrometer 60, a coupler 70, and the polarization maintaining fiber 10 having at least one long period grating 80 disposed therein. A reflector 100 is placed at the fiber endface to reflect light back toward the spectrometer 60. A long period grating signature produced by this arrangement is shown in FIG. 1C.

Figure 2:
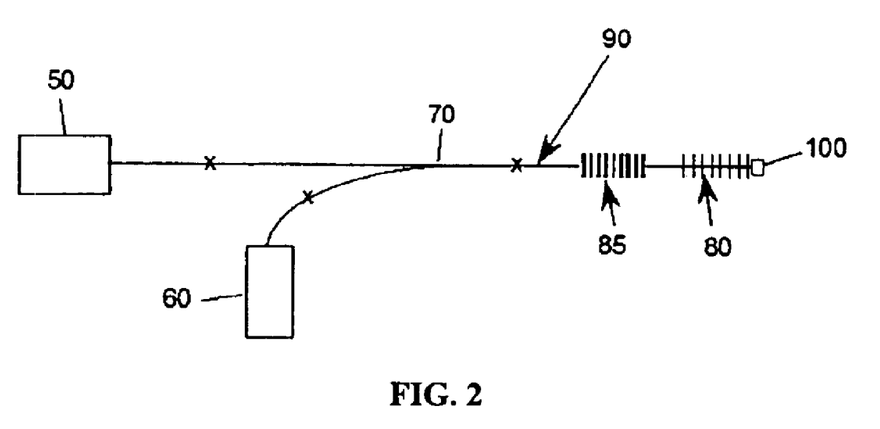
FIG. 2 depicts an optical fiber arrangement that employs a single mode optical fiber having two long period gratings disposed therein.

In another embodiment of the invention, depicted in FIG. 2, a single-mode optical fiber 90 having at least two long period gratings 80, 85 disposed therein is employed as the sensing device. Light is launched from the optical source 50. Each long period grating 80, 85 couples the light into a different order cladding mode. Thus, a first cladding mode that is a higher order cladding mode will extend further out of the optical fiber than a second cladding mode. For example, a first long period grating 80 will generate a first cladding mode, and a second long period grating 85 will generate a second cladding mode. A reflector 100 is positioned on the fiber endface. Reflected light is coupled back into a spectrometer 60 by a coupler 70 where it is detected. Each long period grating will generate its own long period grating signature. This signature is similar to that shown in FIG. 1C. To monitor insitu reactions, the optical fiber has at least one reactive coating disposed thereon proximate to each long period grating. Simultaneous measurements of various parameters are made in real time as the material reacts with the reactive coating. As the reaction proceeds, each LPG peak shifts based on spatially resolvable density changes occurring within the material.

Figure 3:
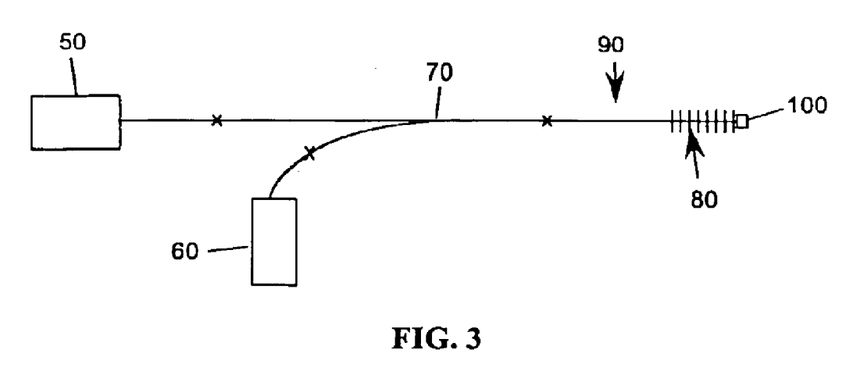
FIG. 3 depicts the optical arrangement employed when a plurality of evanescent field depths result from one long period grating exciting at least two cladding modes.

In an alternative embodiment, a plurality of evanescent field depths result from one long period grating exciting at least two cladding modes. FIG. 3 depicts the optical arrangement for this embodiment. As light is launched from an optical source 50 through a single-mode optical fiber 90 having a long period grating 80 disposed therein, the long period grating 80 simultaneously excites at least two cladding modes (not shown). A first cladding mode is a higher order cladding mode that extends further out of the optical fiber than a second cladding mode. Thus one long period grating 80 simultaneously produces a long period grating signature based on the first and second cladding modes. The reflector 100, reflects light from these modes and the light is coupled into a spectrometer 60 by a coupler 70 to produce the long period grating signature. This signature is similar to that shown in FIG. 1C. To monitor insitu reactions, the optical fiber has at least one reactive coating disposed thereon proximate to the long period grating. Simultaneous parameter measurements are made in real time as the material reacts with the reactive coating. As the reaction proceeds, each LPG peak shifts based on spatially resolvable density changes occurring within the material.

Figure 4:
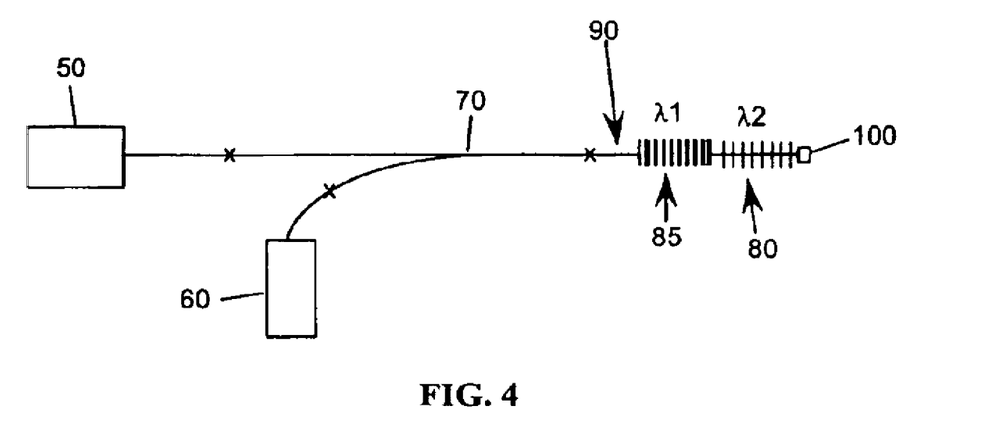
FIG. 4 depicts an optical arrangement employing a single mode optical fiber having two different long period gratings disposed therein, each long period grating is tuned to a different wavelength.

FIG. 4 depicts an optical arrangement for another embodiment of the invention. In this embodiment, a plurality of evanescent field depths result by using at least two long period gratings 80, 85 disposed within a single-mode optical fiber 90 to couple light through a coupler 70 at different wavelengths $\lambda_1$, $\lambda_2$. Light is launched from an optical source 50. Each long period grating couples light at a different wavelength to simultaneously produce two different long period grating signatures. The reflector 100 reflects light back through the fiber such that it is detected by the spectrometer 60. The long period grating signatures are similar to those shown in FIG. 1C. To monitor insitu reactions, the optical fiber has at least one reactive coating disposed thereon proximate to each long period grating. Simultaneous measurements are made in real time as the material reacts with the reactive coating. As the reaction proceeds, each LPG peak shifts based on spatially resolvable density changes occurring within the material.

Figure 5:
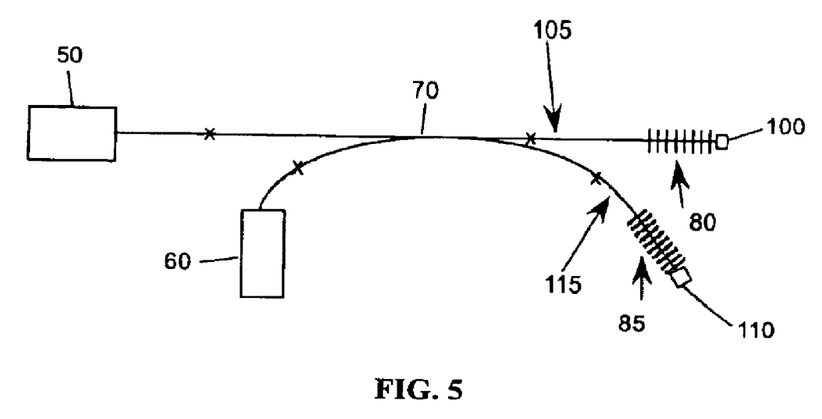
FIG. 5 depicts an optical sensor arrangement where more than one optical fiber is employed.

More than one optical fiber may be employed when practicing the method of the present invention as shown in FIG. 5. In this instance, each optical fiber 105, 115 has at least one long period grating 80, 85 disposed therein and terminates with a reflector 100, 110. For insitu reactions each optical fiber 105, 115 has at least one reactive coating disposed thereon proximate to at least one long period grating (not shown). A first cladding mode that is a higher order cladding mode extends further out of a first optical fiber than a second cladding mode extending out of a second optical fiber. The reflected light is coupled through a coupler 70 into a spectrometer 60 where the long period grating in each fiber 105, 115 produces a long period grating signature. Thus, each long period grating couples light at a specific wavelength to simultaneously produce its own long period grating signature similar to that shown in FIG. 1C. To monitor insitu reactions, each optical fiber has at least one reactive coating disposed thereon proximate to the long period grating. Simultaneous multiple parameter measurements are made in real time as the material reacts with the reactive coating. As the reaction proceeds, each LPG peak shifts based on spatially resolvable density changes occurring within the material.

When it is desirable to make thickness measurements or measure thickness changes in a material, there is no need for a reactive coating to be placed on the optical fiber. In this case, an optical fiber sensor having at least one long period grating disposed therein is provided. An excitation is created in the optical fiber sensor resulting in a plurality of evanescent field sensing depths such that at least two long period grating signatures result. Each long period grating signature is defined by the equation:

$$\lambda = (n_g - n_{cl})\Lambda$$

wherein:

$\lambda$=coupling wavelength for a specific loss band
$\Lambda$=grating period
$n_g$=effective index of the guided mode of the optical fiber
$n_{cl}$=effective index of a cladding mode of the optical fiber.

As the optical fiber sensor is exposed to at least one material, changes in the material as it is applied to the surface of the optical fiber sensor are identified by simultaneously measuring and comparing shifts in each long period grating signature; correlating the shifts to the changes in the material; and solving a series of equations that compare changes in the coupling wavelength for a specific loss band.

In practicing the method of the present invention, the optical fiber sensor is exposed to at least one material. Preferably the material is selected from the group consisting of: a biological sample; a heterogeneous mixture; and a homogeneous chemical sample. Examples of a biological sample include but are not limited to: whole blood; serum; a grain mixture; a slurry; milk; urine; saliva; and spinal fluid.

In cases where there is a reactive coating disposed on the optical fiber sensor, changes in the reactive coating as it reacts with the material are identified by simultaneously measuring and comparing shifts in each long period grating signature. The shifts are correlated to changes in the material. Any change may be identified but, in particular, such changes in the material are spatially resolvable density changes. Preferably, the spatially resolvable density changes are selected from the group consisting of: conformational changes; bound mass changes; thickness measurements; hydrogel swelling; polymer characterization; molecular reactions; polymerization reactions; molecular degradation; polymeric degradation; and thickness changes.

A series of equations are solved to compare changes in the coupling wavelength for a specific loss band. The series of equations consist of at least two equations expressed as:

$$[A]\Delta_{P1}+[B]\Delta_{P2}=\Delta\lambda_1$$

$$[C]\Delta_{P1}+[D]\Delta_{P2}=\Delta\lambda_2$$

wherein:

[A] is a coefficient for a first parameter that reflects the change in wavelength $[\delta\lambda]_1$ per a change in the first parameter $[\delta P_1]_1$ at a first sensing depth and is expressed as:

$$\frac{[\delta\lambda]_1}{[\delta P_1]_1};$$

[B] is a coefficient for a second parameter that reflects the change in wavelength $[\delta\lambda]_1$ per a change in the second parameter $[\delta P_2]_1$ at a first sensing depth and is expressed as:

$$\frac{[\delta\lambda]_1}{[\delta P_2]_1};$$

[C] is a coefficient for a third parameter that reflects the change in wavelength $[\delta\lambda]_2$ per a change in the first parameter $[\delta P_1]_2$ at a second sensing depth and is expressed as:

$$\frac{[\delta\lambda]_2}{[\delta P_1]_2};$$

[D] is a coefficient for a fourth parameter that reflects the change in wavelength $[\delta\lambda]_2$ per a change in the second parameter $[\delta P_2]_2$ at a second sensing depth and is expressed as:

$$\frac{[\delta\lambda]_2}{[\delta P_2]_2};$$

$\Delta_{P1}$ is a first spacially resolvable density change;

$\Delta_{P2}$ is a second spacially resolvable density change;

$\Delta\lambda_1$ is a change in a first coupling wavelength for a specific loss band when the optical fiber sensor is exposed to at least one material; and $\Delta\lambda_2$ is a change in a second coupling wavelength for a specific loss band when the optical fiber sensor is exposed to at least one material.

The first and second spacially resolvable density changes, P1 and P2, are preferably selected from the group consisting of: conformational changes; bound mass changes; thickness measurements; hydrogel swelling; polymer characterization; molecular reactions; polymerization reactions; molecular degradation; polymeric degradation; and thickness changes.

A most preferred method for practicing the present invention is described as follows. An optical fiber sensor comprising at least one polarization preserving fiber having at least one long period grating disposed therein and having at least one reactive coating disposed thereon proximate to the long period grating is provided.

An excitation is created in the optical fiber sensor by launching light through the polarization preserving fiber. At least two long period grating signatures create a plurality of evanescent field sensing depths. Each long period grating signature is defined by the equation:

$$\lambda=(n_g-n_{cl})\Lambda$$

wherein:

$\lambda$=coupling wavelength for a specific loss band $\Lambda$=grating period $n_g$=effective index of the guided mode of the optical fiber $n_{cl}$=effective index of a cladding mode of the optical fiber.

The optical fiber sensor is exposed to at least one material. Changes in the reactive coating as it reacts with the material are identified by measuring and comparing shifts in each long period grating signature; correlating the shifts to the changes in the material; and solving a series of equations that compare changes in the coupling wavelength for a specific loss band.

The series of equations consist of at least two equations expressed as:

$$[A]\Delta_{P1}+[B]\Delta_{P2}=\Delta\lambda_1$$

$$[C]\Delta_{P1}+[D]\Delta_{P2}=\Delta\lambda_2$$

wherein:

[A] is a coefficient for a first parameter that reflects the change in wavelength $[\delta\lambda]_1$ per a change in the first parameter $[\delta P_1]_1$ at a first sensing depth and is expressed as:

$$\frac{[\delta\lambda]_1}{[\delta P_1]_1};$$

[B] is a coefficient for a second parameter that reflects the change in wavelength $[\delta\lambda]_1$ per a change in the second parameter $[\delta P_2]_1$ at a first sensing depth and is expressed as:

$$\frac{[\delta\lambda]_1}{[\delta P_2]_1};$$

[C] is a coefficient for a third parameter that reflects the change in wavelength $[\delta\lambda]_2$ per a change in the first parameter $[\delta P_1]_2$ at a second sensing depth and is expressed as:

$$\frac{[\delta\lambda]_2}{[\delta P_1]_2};$$

[D] is a coefficient for a fourth parameter that reflects the change in wavelength $[\delta\lambda]_2$ per a change in the second parameter $[\delta P_2]_2$ at a second sensing depth and is expressed as:

$$\frac{[\delta\lambda]_2}{[\delta P_2]_2};$$

$\Delta_{P1}$ is a first spacially resolvable density change;

$\Delta_{P2}$ is a second spacially resolvable density change;

$\Delta\lambda_1$ is a change in a first coupling wavelength for a specific loss band when the optical fiber sensor is exposed to at least one material; and Δλ₂ is a change in a second coupling wavelength for a specific loss band when the optical fiber sensor is exposed to at least one material.

An optical fiber sensor arrangement for practicing the method of the present invention where simultaneous multiple parameter measurements are made comprises at least one optical fiber having at least one long period grating disposed therein and having at least one reactive coating disposed thereon proximate to the long period grating. A source means for launching light through the optical fiber is provided such that a plurality of evanescent field sensing depths result. A detector for detecting a coupling wavelength for a specific loss band is also provided. The coupling wavelength is defined by the equation:

$$\lambda = (n_g - n_{cl})\Lambda$$

wherein:
$\lambda$=coupling wavelength for a specific loss band
$\Lambda$=grating period
$n_g$=effective index of the guided mode of the optical fiber
$n_{cl}$=effective index of a cladding mode of the optical fiber.

The arrangement also has a means for solving a series of equations that compare changes in the coupling wavelength for a specific loss band.

The optical fiber employed in the sensor arrangement is preferably a polarization preserving fiber; a single-mode optical fiber having one long period grating disposed therein; or a single-mode optical fiber having at least two long period gratings disposed therein.

Alternatively, the optical fiber sensor comprises at least two optical fibers. Each optical fiber has at least one long period grating disposed therein and each has at least one reactive coating disposed thereon proximate to the long period grating. The long period grating couples light at a specific wavelength. A first long period grating couples light into a first cladding mode and a second long period grating couples light into a higher order second cladding mode. The light coupled into the higher order second cladding mode extends further out of the optical fiber than the light coupled into the first order cladding mode.

EXAMPLES

Example 1

Figure 6A:
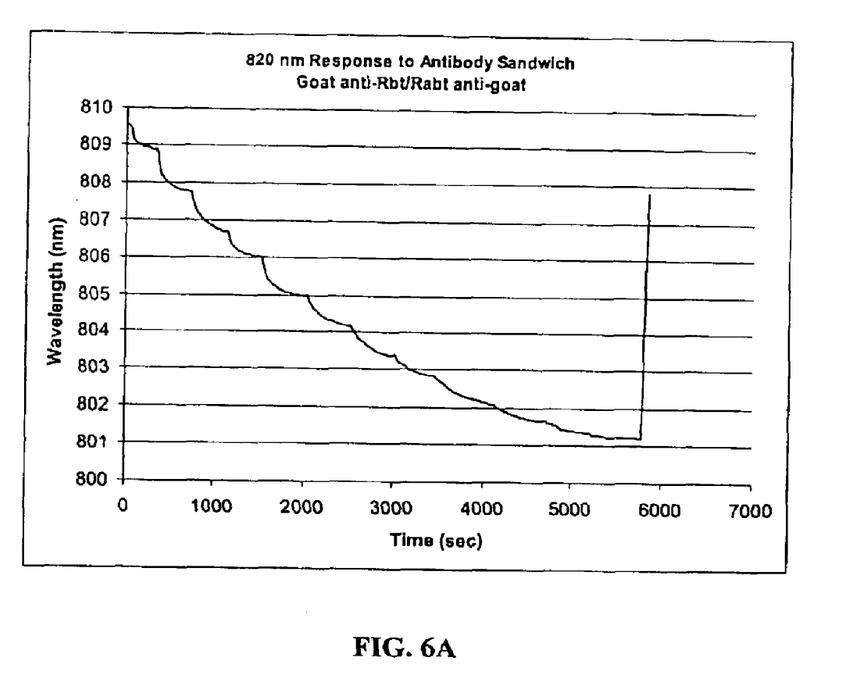
FIG. 6A depicts the response decay for anti-rabbit/rabbit anti-goat antibody binding for an 820 nm system.
Figure 6B:
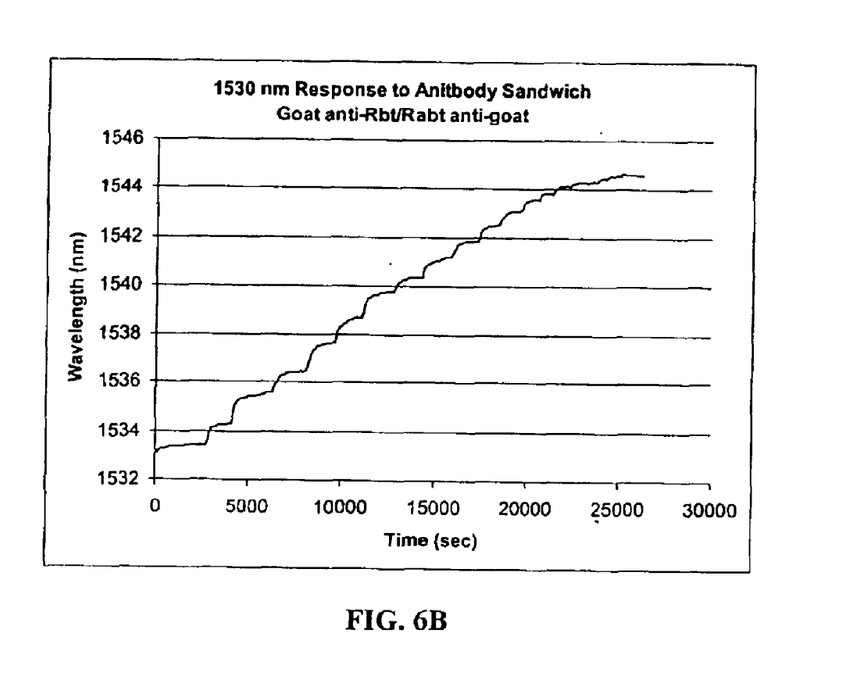
FIG. 6B depicts the response decay for anti-rabbit/rabbit anti-goat antibody binding for a 1530 nm system.

To demonstrate different sensing field depths for different wavelengths, tests were performed through sandwiching of IgG antibodies. To experimentally determine sensing depts. For the various long period grating (LPG) sensors, antibody sandwich layers were applied to the LPG sensor until there was no minimal shift in wavelength (1/e point). The LPG was constructed with a 69 micron period for the 820 nm response and a 136 micron period for the 1530 nm sensor. Fibers were prepared using a methanol wash for one hour and were then silated with aminopropylsilane. A goat-anti-rabbit antibody was covalently attached through EDAC chemistry. Alternating layers of goat-anti-rabbit and rabbit-anti-goat were then applied by exposing the fibers to samples at 100 μg/ml. FIG. 6A depicts the response decay for anti-rabbit/rabbit anti-goat antibody binding for the 820 nm system and FIG. 6B depicts the response decay for the 1530 nm system. The 820 nm systems illustrates 12 layers for antibody binding before the wavelength shift reaches the 1/e point. The 1530 nm system illustrates 16 layers before the wavelength shift reaches the 1/e point, as shown in FIG. 6B. This data can be used to give a theoretical difference in sensing depth between 1530 nm and 820 nm of 25%.

Example 2

The method of the present invention was employed to measure thickness on a cylindrical object by long period grating (LPG) changes in thin film coating systems. To measure the sensing depth of the sensor, an ionically self-assembled monolayer (ISAM) coating process consisting of alternating layers of cations and anions was employed. Poly(diallyldimethyl ammonium choloride) (PDDA) and Poly(sodium 4 styrenesulfonate) (PSS) were selected for their stability between wet and dry states. In order to verify the thickness of each bilayer, several silicon wafers were cleaned and varying ISAM layers were applied to the wafer. Measurements were made using an ellipsometer. The following procedure was used to coat 40, 70, and 90 bilyaers on three different slides. Thickness was then measured using an ellipsometer. Once measurements were taken, the same procedure was used to coat the LPG sensors to determine the evanescent sensing depths.

All wafers/sensors were initially cleaned using an alkaline solution (di-$H_2O$: Concentrated HCl: 30% $H_2O_2$ in a 5:5:1 ratio) for 15 minutes with sonication.

After cleaning, the wafers/sensors were dipped in solutions of Poly(diallyldimethyl ammonium chloride) (PDDA) (available from Aldrich Chemical Company), 1% by weight in $H_2O$ with a pH of 5.5 and Poly(sodium 4 styrenesulfonate) (PSS) (available from Aldrich Chemical Company), 2% by weight in $H_2O$ with a pH of 6.85 in an alternating fashion for 30 seconds under agitation to build up the coating thickness.

The following table illustrates the thickness changes in the ISAM bilayers. The thickness increases linearly with the number of applied bilayers. These measurements were used to correlate back to the LPG sensing depth measurements.

| Ellipsometer Measurements on ISAM Coated Silicon Wafers | |
| --- | --- |
| Number of Bilayers | Average Thickness (nm) |
| 40 | 88.821 |
| 70 | 156.425 |
| 90 | 197.505 |

Figure 7:
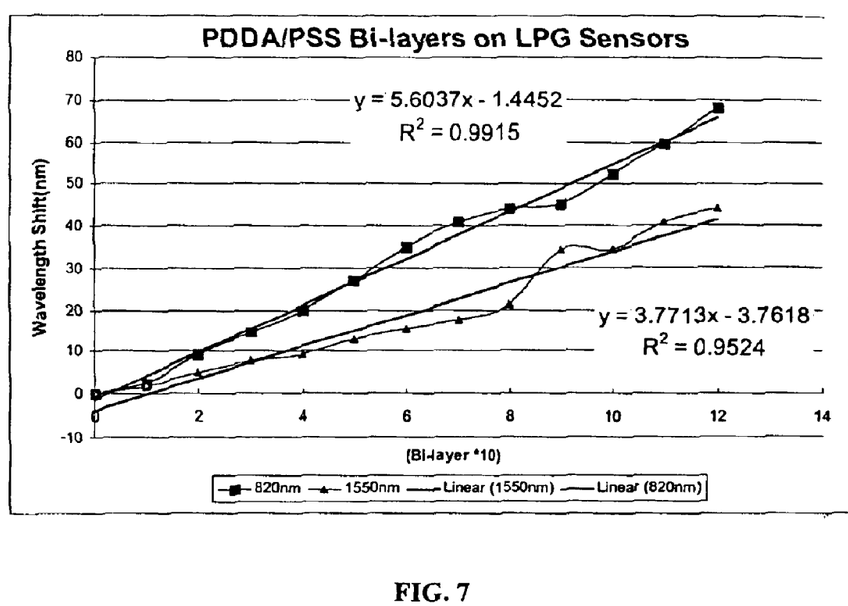
FIG. 7 is a graph of the effective refractive index as bilayers are built-up on a long period grating sensor.

The information from these measurements was used to determine the thickness of the LPG sensing field by building up the bilayers on the sensor and watching the shift in wavelength as the sensor senses a different effective refractive index. The experimental difference between the two wavelengths of operation is 25% and is shown in FIG. 7.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A fiber-optic method for making simultaneous multiple parameter measurements, the method comprising the steps of:
    a) providing an optical fiber sensor comprising at least one optical fiber having at least one long period grating disposed therein and having at least one reactive coating disposed thereon proximate to the at least one long period grating;
    b) creating an excitation in the optical fiber sensor wherein a plurality of evanescent field sensing depths result, creating at least two long period grating signatures, wherein each long period grating signature is defined by the equation:

$$\lambda = (ng - ncl)\Lambda$$

wherein:
λ=coupling wavelength for a specific loss band
Λ=grating period
ng=effective index of the guided mode of the optical fiber
ncl=effective index of a cladding mode of the optical fiber;

c) exposing the optical fiber sensor to at least one material; and d) identifying changes in the reactive coating as it reacts with the material by measuring and comparing shifts in each long period grating signature; correlating the shifts to the changes in the material; and solving a series of equations that compare changes in the coupling wavelength for a specific loss band wherein the series of equations consist of at least two equations expressed as:

$$[A]\Delta_{P1} + [B]\Delta_{P2} = \Delta\lambda_1$$
$$[C]\Delta_{P1} + [D]\Delta_{P2} = \Delta\lambda_2$$

wherein:

[A] is a coefficient for a first parameter that reflects the change in wavelength $[\delta\lambda]_1$ per a change in the first parameter $[\delta P_1]_1$ at a first sensing depth and is expressed as:

$$\frac{[\delta\lambda]_1}{[\delta P_1]_1};$$

[B] is a coefficient for a second parameter that reflects the change in wavelength $[\delta\lambda]_1$ per a change in the second parameter $[\delta P_2]_1$ at a first sensing depth and is expressed as:

$$\frac{[\delta\lambda]_1}{[\delta P_2]_1};$$

[C] a coefficient for a third parameter that reflects the change in wavelength $[\delta\lambda]_2$ per a change in the first parameter $[\delta P_1]_2$ at a second sensing depth and is expressed as:

$$\frac{[\delta\lambda]_2}{[\delta P_1]_2};$$

[D] is a coefficient for a fourth parameter that reflects the change in wavelength $[\delta\lambda]_2$ per a change in the second parameter $[\delta P_2]_2$ at a second sensing depth and is expressed as:

$$\frac{[\delta\lambda]_2}{[\delta P_2]_2};$$

$\Delta_{P1}$ is a first spacially resolvable density change;
$\Delta_{P2}$ is a second spacially resolvable density change;
$\Delta\lambda_1$ is a change in a first coupling wavelength for a specific loss band when the optical fiber sensor is exposed to at least one material; and $\Delta\lambda_2$ is a change in a second coupling wavelength for a specific loss band when the optical fiber sensor is exposed to at least one material.

2. A fiber-optic method according to claim 1, wherein the optical fiber is a polarization preserving fiber and wherein the plurality of evanescent field depths result from light launched through the polarization preserving fiber.

3. A fiber-optic method according to claim 2, wherein the changes in the material are spatially resolvable density changes.

4. A fiber-optic method according to claim 3, wherein the spatially resolvable density changes are selected from the group consisting of: conformational changes; bound mass changes; thickness measurements; hydrogel swelling; polymer characterization; molecular reactions; polymerization reactions; molecular degradation polymeric degradation; and thickness changes.

5. A fiber-optic method according to claim 1, wherein the plurality of evanescent field depths result from light launched through single-mode optical fiber having at least two long period gratings disposed therein wherein each long period grating couples into a different order cladding mode.

6. A fiber-optic method according to claim 5, comprising a first cladding mode that is a higher order cladding mode extending further out of the optical fiber than a second cladding mode and wherein a long period grating signature is produced by each long period grating.

7. A fiber-optic method according to claim 6, wherein the changes in the material are spatially resolvable density changes.

8. A fiber-optic method according to claim 7, wherein the spatially resolvable density changes are selected from the group consisting of: conformational changes; bound mass changes; thickness measurements; hydrogel swelling; polymer characterization molecular reactions; polymerization reactions; molecular degradation; polymeric degradation and thickness changes.

9. A fiber-optic method according to claim 1, wherein the plurality of evanescent field depths result from light launched through single-mode optical fiber having a long period grating disposed therein and wherein the long period grating excites at least two cladding modes.

10. A fiber-optic method according to claim 9, comprising a first cladding mode that is a higher order cladding mode extending further out of the optical fiber than a second cladding mode and wherein a long period grating signature is produced by the long period grating.

11. A fiber-optic method according to claim 10, wherein the changes in the material are spatially resolvable density changes.

12. A fiber-optic method according to claim 11, wherein the spatially resolvable density changes are selected from the group consisting of: conformational changes; bound mass changes; thickness measurements; hydrogel swelling; polymer characterization; molecular reactions; polymerization reactions; molecular degradation; polymeric degradation; and thickness changes.

13. A fiber-optic method according to claim 1, wherein the plurality of evanescent field depths result from light launched through single-mode optical fiber having at least two long period gratings disposed therein wherein each long period grating couples light at a different wavelength.

14. A fiber-optic method according to claim 13, wherein the changes in the material are spatially resolvable density changes.

15. A fiber-optic method according to claim 14, wherein the spatially resolvable density changes are selected from the group consisting of: conformational changes; bound maas changes; thickness measurements; hydrogel swelling; polymer characterization; molecular reactions; polymerization reactions; molecular degradation; polymeric degradation; and thickness changes.

16. A fiber-optic method according to claim 1, wherein the fiber-optic sensor comprises at least two optical fibers, each optical fiber having at least one long period grating disposed therein and each optical fiber having at least one reactive coating disposed thereon proximate to the at least one tong period grating wherein each long period grating couples light at a specific wavelength.

17. A fiber-optic method according to claim 16, wherein a first cladding mode that is a higher order cladding mode extends further out of a first optical fiber than a second cladding mode extending from a second optical fiber and wherein a long period grating signature is produced by each long period grating.

18. A fiber-optic method according to claim 16, wherein the changes in the material are spatially resolvable density changes.

19. A fiber-optic method according to claim 18, wherein the spatially resolvable density changes are selected from the group consisting of conformational changes; bound mass changes; thickness measurements; hydrogel swelling; polymer characterization; molecular reactions; polymerization reactions; molecular degradation; polymeric degradation; and thickness changes.

20. A fiber-optic method according to claim 1, wherein the material is selected from the group consisting of: a biological sample; a heterogenous mixture; and a homogenous chemical sample.

21. A fiber-optic method according to claim 20, wherein the biological sample is selected from the group consisting of: whole blood; serum; a grain mixture; a slurry; milk; urine; saliva; and spinal fluid.

22. A fiber-optic method according to claim 1, wherein P1 is selected from the group consisting of: conformational changes; bound mass changes; thickness measurements; hydrogel swelling; polymer characterization; molecular reactions; polymerization reactions; molecular degradation; polymeric degradation; and thickness changes.

23. A fiber-optic method according to claim 1, wherein P2 is selected from the group consisting of: conformational changes; bound mass changes; thickness measurements; hydrogel swelling; polymer characterization; molecular reactions; polymerization reactions; molecular degradation; polymeric degradation; and thickness changes.

24. A fiber-optic method for making simultaneous multiple parameter measurements, the method comprising the steps of
a) providing an optical fiber sensor comprising at least one optical fiber having at least one long period grating disposed therein;
b) creating an excitation in the optical fiber sensor wherein a plurality of evanescent field sensing depths result, creating at least two long period grating signatures, wherein each long period grating signature is defined by the equation:

$$\lambda = (n_g - n_{cl})\Lambda$$

wherein:
$\lambda$ = coupling wavelength for a specific loss band
$\Lambda$ = grating period
$n_g$ = effective index of the guided mode of the optical fiber
$n_{cl}$ = effective index of a cladding mode of the optical fiber;

c) exposing the optical fiber sensor to at least one material; and
d) identifying changes in the material as it is applied to a surface of the optical fiber sensor by measuring and comparing shifts in each long period grating signature; correlating the shifts to the changes in the material; and solving a series of equations that compare changes in the coupling wavelength for a specific loss band wherein the series of equations consist of at least two equations expressed as:

$$[A]\Delta_{P1} + [B]\Delta_{P2} = \Delta\lambda_1$$

$$[C]\Delta_{P1} + [D]\Delta_{P2} = \Delta\lambda_2$$

wherein:
[A] is a coefficient for a first parameter that reflects the change in wavelength $[\delta\lambda]_1$ per a change in the first parameter $[\delta P_1]_1$ at a first sensing depth and is expressed as:

$$\frac{[\delta\lambda]_1}{[\delta P_1]_1};$$

[B] is a coefficient for a second parameter that reflects the change in wavelength $[\delta\lambda]_1$ per a change in the second parameter $[\delta P_2]_1$ at a first sensing depth and is expressed as:

$$\frac{[\delta\lambda]_1}{[\delta P_2]_1};$$

[C] is a coefficient for a third parameter that reflects the change in wavelength $[\delta\lambda]_2$ per a change in the first parameter $[\delta P_1]_2$ at a second sensing depth and is expressed as:

$$\frac{[\delta\lambda]_2}{[\delta P_1]_2};$$

[D] is a coefficient for a fourth parameter that reflects the change in wavelength $[\delta\lambda]_2$ per change in the second parameter $[\delta P_2]_2$ at a second sensing depth and is expressed as:

$$\frac{[\delta\lambda]_2}{[\delta P_2]_2};$$

$\Delta_{P1}$ is a first spacially resolvable density change;
$\Delta_{P2}$ is a second spacially resolvable density change;
$\Delta\lambda_1$ is a change in a first coupling wavelength for a specific loss band when the optical fiber sensor is exposed to at least one material; and
$\Delta\lambda_2$ is a change in a second coupling wavelength for a specific loss band when the optical fiber sensor is exposed to at least one material.

25. A fiber-optic method according to claim 24, wherein the change in the material is a thickness measurement or a thickness change.

26. A fiber-optic method for making simultaneous multiple parameter measurements, the method comprising the steps of:
a) providing an optical fiber sensor comprising at least one polarization preserving fiber having at least one long period grating disposed therein and having at least one reactive coating disposed thereon proximate to the long period grating;

b) creating an excitation in the optical fiber sensor by launching light through the polarization preserving fiber wherein a plurality of evanescent field sensing depths result, creating at least two long period grating signatures, wherein each long period grating signature is defined by the equation:

$$\lambda=(n_g-n_{cl})\Lambda$$

wherein:
$\lambda$=coupling wavelength for a specific loss band
$\Lambda$=grating period
$n_g$=effective index of the guided mode of the optical fiber
$n_{cl}$=effective index of a cladding mode of the optical fiber;

c) exposing the optical fiber sensor to at least one material; and d) identifying changes in the reactive coating as it reacts with the material by measuring and comparing shifts in each long period grating signature; correlating the shifts to the changes in the material; and solving a series of equations that compare changes in the coupling wavelength for a specific loss band; wherein the series of equations consist of at least two equations expressed as:

$$[A]\Delta_{P1}+[B]\Delta_{P2}=\Delta\lambda_1$$

$$[C]\Delta_{P1}+[D]\Delta_{P2}=\Delta\lambda_2$$

wherein:
[A] is a coefficient for a first parameter that reflects the change in wavelength $[\delta\lambda]_1$ per a change in the first parameter $[\delta P_1]_1$ at a first sensing depth and is expressed as:

$$\frac{[\delta\lambda]_1}{[\delta P_1]_1};$$

[B] is a coefficient for a second parameter that reflects the change in wavelength $[\delta\lambda]_1$ per a change in the second parameter $[\delta P_2]_1$ at a first sensing depth and is expressed as:

$$\frac{[\delta\lambda]_1}{[\delta P_2]_1};$$

[C] is a coefficient for a third parameter that reflects the change in wavelength $[\delta\lambda]_2$ per a change in the first parameter $[\delta P_1]_2$ at a second sensing depth and is expressed as:

$$\frac{[\delta\lambda]_2}{[\delta P_1]_2};$$

[D] is a coefficient for a fourth parameter that reflects the change in wavelength $[\delta\lambda]_2$ per a change in the second parameter $[\delta P_2]_2$ at a second sensing depth and is expressed as:

$$\frac{[\delta\lambda]_2}{[\delta P_2]_2};$$

$\Delta_{P1}$ is a first specially resolvable density change;
$\Delta_{P2}$ is a second specially resolvable density change;
$\Delta\lambda_1$ is a change in a first coupling wavelength for a specific loss band when the optical fiber sensor is exposed to at least one material; and
$\Delta\lambda_2$ is a change in a second coupling wavelength for a specific loss band when the optical fiber sensor is exposed to at least one material.

27. An optical fiber sensor arrangement for making simultaneous multiple parameter measurements comprising:
at least one optical fiber having at least one long period grating disposed therein and having at least one reactive coating disposed thereon proximate to the long period grating;
a source means for launching light through the optical fiber wherein a plurality of evanescent field sensing depths result;
a detector for detecting a coupling wavelength for a specific loss band, wherein the coupling wavelength is defined by the equation:

$$\lambda=(n_g-n_{cl})\Lambda$$

wherein:
$\lambda$=coupling wavelength for a specific loss band
$\Lambda$=grating period
$n_g$=effective index of the guided mode of the optical fiber
$n_{cl}$=effective index of a cladding mode of the optical fiber; and
a means for solving a series of equations that compare changes in the coupling wavelength for a specific loss band.

28. An optical fiber sensor arrangement according to claim 27, wherein the optical fiber is a polarization preserving fiber, wherein a plurality of evanescent field depths result from light launched through tho polarization preserving fiber.

29. An optical fiber sensor arrangement according to claim 27, wherein the optical fiber is single-mode optical fiber having one long period grating disposed therein wherein the long period grating excites at least two cladding modes.

30. An optical fiber sensor arrangement according to claim 27, wherein the optical fiber is a single-mode optical fiber having at least two long period gratings disposed therein and wherein each long period grating couples into a different order cladding mode.

31. An optical fiber sensor arrangement according to claim 30, wherein a first long period grating couples light into a first cladding mode and wherein a second long period grating couples light into a higher order second cladding mode and wherein the light coupled into the higher order second cladding mode extends further out of the optical fiber than the light coupled into the first cladding mode.

32. An optical fiber sensor arrangement according to claim 27, wherein the optical fiber sensor comprises at least two optical fibers, each optical fiber having at least one long period grating disposed therein and each optical fiber having at least one reactive coating disposed thereon proximate to the long period grating, wherein each long period grating couples light at a specific wavelength and wherein a first long period grating couples light into a first cladding mode and wherein a second long period grating couples light into a higher order second cladding mode and wherein the light coupled into the higher order second cladding mode extends further out of the optical fiber than the light coupled into the first cladding mode.

* * * * *